United States Patent [19]

Mishima et al.

[11] 4,192,953
[45] Mar. 11, 1980

[54] POLYPRENYL DERIVATIVES

[75] Inventors: Hiroshi Mishima; Akira Ogiso; Shinsaku Kobayashi, all of Tokyo, Japan

[73] Assignee: Sankyo Company Limited, Tokyo, Japan

[21] Appl. No.: 1,162

[22] Filed: Jan. 4, 1979

Related U.S. Application Data

[62] Division of Ser. No. 807,913, Jun. 20, 1977, abandoned, which is a division of Ser. No. 633,097, Nov. 18, 1975, Pat. No. 4,059,641.

[51] Int. Cl.$^2$ .................. C07C 43/00; C07C 43/02; A61K 31/08; A61K 31/07
[52] U.S. Cl. .................. 568/673; 568/687; 568/675; 424/313; 575/314; 560/81; 560/83; 560/89; 560/95; 560/103; 560/190; 560/198; 560/201; 560/205; 560/225; 560/263
[58] Field of Search .................. 568/673, 675, 687; 560/64, 81, 83, 89, 95, 103, 104, 105, 113, 190, 198, 201, 205, 224, 225, 261, 262, 263; 260/410.6

[56] References Cited

U.S. PATENT DOCUMENTS 3,665,040  5/1972  Rueff et al. .................. 568/687

*Primary Examiner*—Howard T. Mars

*Attorney, Agent, or Firm*—Frishauf, Holtz, Goodman & Woodward

[57] ABSTRACT

Polyprenyl derivatives having the formula

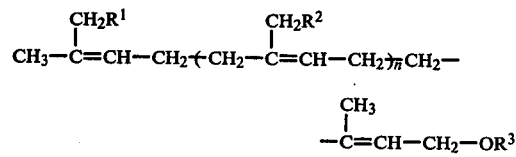

in which $R^1$ and $R^2$ may be the same or different and each represents hydrogen atom, hydroxyl group, an alkoxy group having 1–8 carbon atoms, an aliphatic acyloxy group having 2–18 carbon atoms, an aromatic acyloxy group or an araliphatic acyloxy group having 2–3 carbon atoms in the aliphatic acyl moiety, $R^3$ represents hydrogen atom, an alkyl group having 1–8 carbon atoms, an aliphatic acyl group having 2–18 carbon atoms, an aromatic acyl group or an araliphatic acyl group having 2–3 carbon atoms in the aliphatic acyl moiety, n is an integer of 1–4 and, when n is an interger of 2–4, $R^2$'s may be the same or different; provided that, when n is 1 or 2, at least one of $R^2$ and $R^2$'s is hydroxyl group, an alkoxy group, an aliphatic acyloxy group, an aromatic acyloxy group or an araliphatic acyloxy group. These derivatives are useful as medicines for treating peptic ulcer.

6 Claims, No Drawings

POLYPRENYL DERIVATIVES

This is a division of application Ser. No. 807,913, filed June 20, 1977, now abandoned, which, in turn, is a division of Ser. No. 633,097, filed Nov. 18, 1975, which issued as U.S. Pat. No. 4,059,641.

This invention relates to novel polyprenyl derivatives. More particularly, this invention relates to polyprenyl derivatives having the formula

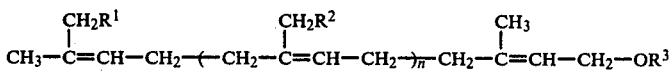

in which $R^1$ and $R^2$ may be the same or different and each represents hydrogen atom, hydroxyl group, an alkoxy group having 1–8 carbon atoms, an aliphatic acyloxy group having 2–18 carbon atoms, an aromatic acyloxy group or an araliphatic acyloxy group having 2–3 carbon atoms in aliphatic acyl moiety, $R^3$ represents hydrogen atom, an alkyl group having 1–8 carbon atoms, an aliphatic acyl group having 2–8 carbon atoms, an aromatic acyl group or an araliphatic acyl group having 2–3 carbon atoms in aliphatic acyl moiety, and n is an integer of 1–4; and when n is an integer of 2–4, $R^2$'s may be the same or different, and when n is 1 or 2, at least one of $R^1$ and $R^2$'s is hydroxyl group, an alkoxy group, an aliphatic acyloxy group, an aromatic acyloxy group or an araliphatic acyloxy group.

The polyprenyl derivatives (I) according to this invention are of value as medicines for treating peptic ulcer.

In the above-mentioned formula (I), $R^1$ and $R^2$ may be the same or different and each represents hydrogen atom, hydroxyl group, an alkoxy group such as methoxy, ethoxy, n-propoxy, isopropoxy, n-butoxy, isobutoxy, tert-butoxy, pentyloxy, hexyloxy, heptyloxy and octyloxy, an aliphatic acyloxy group such as an alkanoyloxy group, for instance, acetoxy, propionyloxy, butyryloxy, isobutyryloxy, valeryloxy, isovaleryloxy, pivaloyloxy, caproyloxy, 2-methylvaleryloxy, heptanoyloxy, octanoyloxy, 2-ethylhexanoyloxy, nonanoyloxy, decanoyloxy, undecanoyloxy, n-lauroyloxy, myristoyloxy, pentadecanoyloxy, palmitoyloxy and stearoyloxy and an alkenoyloxy group, for instance, acryloyloxy, crotonoyloxy, 3-butenoyloxy, methacryloyloxy, tigloyloxy, sorboyloxy, 10-undecenoyloxy and oleoyloxy, an aromatic acyloxy group such as a benzoyloxy group which may be substituted with an alkyl group having 1–3 carbon atoms, e.g., methyl, ethyl, n-propyl and isopropyl, an alkoxy group having 1–3 carbon atoms, e.g., methoxy, ethoxy, n-propoxy and isopropoxy or a halogen atom, e.g., chlorine, bromine and fluorine, or an araliphatic acyloxy group such as phenylacetoxy, phenylpropionyloxy and cinnamoyloxy.

$R^3$ represents hydrogen atom, an alkyl group such as methyl, ethyl, n-propyl, isopropyl, n-butyl, isobutyl, tert-butyl, pentyl, hexyl, heptyl and octyl, an aliphatic acyl group such as an alkanoyl group, for instance, acetyl, propionyl, butyryl, isobutyryl, valeryl, isovaleryl, pivaloyl, caproyl, 2-methyl-n-valeryl, heptanoyl, octanoyl, 2-ethylhexanoyl, nonanoyl, decanoyl, undecanoyl, lauroyl, myristoyl, pentadecanoyl, palmitoyl and stearoyl and an alkenoyl group, for instance, acryloyl, methacryloyl, crotonoyl, 3-butenoyl, tigloyl, sorboyl, 10-undecenoyl and oleoyl, an aromatic acyl group such as a benzoyl group which may be substituted with an alkyl group having 1–3 carbon atoms, e.g., methyl, ethyl, n-propyl and isopropyl, an alkoxy group having 1–3 carbon atoms, e.g., methoxy, ethoxy, n-propoxy and isopropoxy or a halogen atom, e.g., chlorine, bromine and fluorine, or an aromatic-aliphatic acyl group such as phenylacetyl, phenylpropionyl and cinnamoyl.

The compounds of the formula (I) of the present invention are present in the form of various geometrical isomers depending upon configuration of the double bonds. The compounds stated hereinafter are named according to E, Z expression proposed by IUPAC in The Journal of Organic Chemistry, vol. 35, 2849(1970). The isomers and mixtures of the isomers are inclusively expressed herein by the single formula (I) for convenience' sake, but it should be noted that the single formula (I) is not meant to limit the scope of this invention.

In the prior art, it was reported that geranyl farnesylacetate (Gefarnate) has an anti-ulcer activity (E. Adami et al, Arch. int. Pharmacodyn., 1964, 147, No. 1–2, 113). However, there is an increased demand for a new and improved medicament which is more effective against a wide variety of ulcers, particularly peptic ulcer such as gastric ulcer or duodenal ulcer.

We have for many years been engaged in studies for finding our novel pharmaceuticals by way of isolating a physiologically active ingredient from plants. As a result of our studies, we have isolated a diterpenediol compound, (E, Z, E)-7-hydroxymethyl-3,11,15-trimethyl-2,6,10,14-hexadecatetraen-I-ol, from plants belonging to the genus Croton, particularly Plau-noi (*Croton columnaris* Airy Shans), Plau-luat (*Croton hutchinsonianus* Hosseus) and Plau-yai (*Croton oblongifolius* Roxb.) growing in Thailand and also succeeded in chemical synthesis of this diterpenediol compound as well as its homologs and derivatives. As a further result of our studies, we have unexpectedly found that the above-mentioned diterpenoid compound and its homologes and derivatives, that is, the compounds having the formula (I) are highly effective for treating peptic ulcer with low toxicity. The present invention has been completed upon the aforesaid findings.

It is, accordingly, a primary object of this invention to provide a new group of the polyprenyl derivatives having the above formula (I) which exhibit potent anti-ulcer activity.

According to this invention, there are provided the new polyprenyl derivatives (I) having a utility as medicines for treating peptic ulcer.

Of the polyprenyl derivatives (I), there can be mentioned as a preferable group those compounds having the formula (I) wherein $R^1$ and $R^2$ may be the same or different and each represents hydrogen atom, hydroxyl group, an alkoxy group having 1–4 carbon atoms, an aliphatic acyloxy group having 2–12 carbon atoms, benzoyloxy group or cinnamoyloxy group, $R^3$ represents hydrogen atom, an alkyl group having 1–4 carbon atoms, an aliphatic acyl group having 2–12 carbon atoms, benzoyl group or cinnamoyl group, n is an integer of 1–3 and, when n is 2 or 3, $R^2$'s may be the same or different; provided that, when n is 1 or 2, at least one of $R^1$ and $R^2$'s is hydroxyl group, an alkoxy group, an aliphatic acyloxy group, benzoyloxy group or cinnamoyloxy group.

As a more preferable group of the polyprenyl derivatives (I), there can be mentioned those compounds having the formula (I) wherein $R^1$ represents hydrogen atom, $R^2$ represents hydrogen atom, hydroxyl group, an alkoxy group having 1-4 carbon atoms, an aliphatic acyloxy group having 2-12 carbon atoms, benzoyloxy group or cinnamoyloxy group, $R^3$ represents hydrogen atom, an alkyl group having 1-4 carbon atoms, an aliphatic acyl group having 2-12 carbon atoms, benzoyl group or cinnamoyl group and n is an integer of 1-3; provided that, when n is 1, $R^2$ is the above-defined group other than hydrogen atom and, when n is 2 or 3, at least one of $R^2$'s is the above-defined group other than hydrogen atom.

As the most preferable group of the polyprenyl derivatives (I), there can be mentioned those compounds having the formula (I) wherein $R^1$ represents hydrogen atom, the $R^2$ in the side chain at 7-position of the structural formula represents hydroxyl group, an alkoxy group having 1-2 carbon atoms, an aliphatic acyloxy group having 2-12 carbon atoms, benzoyloxy group or cinnamoyloxy group, $R^3$ represents hydrogen atom, an alkyl group having 1-2 carbon atoms, an aliphatic acyl group having 2-12 carbon atoms, benzoyl group or cinnamoyl group and n is an integer of 1-3.

Activities of the present polyprenyl derivatives suppressing the ulcer are seen from the following comparative pharmacological tests.

(1) ANTI-RESERPINE ULCER ACTIVITY

Test procedures

The test was carried out in accordance with the method described by C. Blackmann, D. S. Campion and F. N. Fastier in British Journal of Pharmacology and Chemotherapy, vol. 14, 112 (1959), which is as follows:

The test compound was intraperitoneally administered to male mice (ddY strains, body weight: 28-33 g), and, 30 minutes later, reserpine was subcutaneously administered in the dose of 10 mg/kg. After 18 hours from the reserpine administration, the animal was sacrificed, and the stomach was isolated. This stomach was inflated with 2 ml of 0.5% formalin and was fixed. Then, the stomach was opened by cutting along the greater curvature, and the ulcer area[1] was measured with a stereoscopic microscope. The ulcer areas of the treated group and the control group were compared, and the inhibitory ratios were calculated.

[1] ulcer area (mm$^2$): sum of each ulcer area (longitude × latitude)

Test results

The anti-reserpine ulcer activity shown when the test compound was intraperitoneally administered is set out in Table 1.

Table 1

| Test Compound | Dose (mg/kg, i.p.) | Number of Mouse | Inhibitory Ratio (%) |
|---|---|---|---|
| Compound A | 100 | 5 | 68.4 |
| Compound B | 100 | 5 | 65.0 |
| Compound C | 100 | 5 | 59.0 |
| Compound D | 127 | 5 | 54.2 |
| Compound E | 171 | 5 | 64.5 |
| Compound F | 220 | 5 | 63.3 |
| Compound G | 109 | 5 | 45.0 |
| Compound H | 100 | 5 | 57.0 |
| Compound I | 127 | 5 | 64.5 |
| Compound J | 100 | 5 | 49.4 |
| Compound K | 100 | 5 | 58.7 |

Table 1-continued

| Test Compound | Dose (mg/kg, i.p.) | Number of Mouse | Inhibitory Ratio (%) |
|---|---|---|---|
| Compound L | 100 | 5 | 55.3 |
| Compound M | 77.8 | 5 | 60.1 |
| Compound N | 105 | 5 | 64.5 |
| Compound O | 122 | 5 | 74.2 |
| Compound P | 150 | 5 | 45.7 |
| Compound Q | 193 | 5 | 56.2 |
| Gefarnate | 100 | 5 | 10.0 |

Compound A: (E,Z,E)-7-hydroxymethyl-3,11,15-trimethyl-2,6,10,14-hexadecatetraen-1-ol Compound B: (E,Z,E) & (E,E,E)-7-hydroxymethyl-3,11,15-trimethyl-2,6,10,14-hexadecatetraen-1-ol Compound C: (E,Z,E), (E,E,E), (Z,Z,E) & (Z,E,E)-7-hydroxymethyl-3,11,15-trimethyl-2,6,10,14-hexadecatetraen-1-ol Compound D: (E,Z,E))-7-hydroxymethyl-3,11,15-trimethyl-2,6,10,14-hexadecatetraen-1-ol diacetate Compound E: (E,Z,E)-7-hydroxymethyl-3,11,15-trimethyl-2,6,10,14-hexadecatetraen-1-ol dibenzoate Compound F: (E,Z,E)-7-hydroxymethyl-3,11,15-trimethyl-2,6,10,14-hexadecatetraen-1-ol dilaurate Compound G: (E,Z,E)-7-hydroxymethyl-3,11,15-trimethyl-2,6,10,14-hexadecatetraen-1-ol dimethyl ether Compound H: (E,E,E)-7-hydroxymethyl-3,11,15-trimethyl-2,6,10,14-hexadecatetraen-1-ol Compound I: (E,E,E)-7-hydroxymethyl-3,11,15-trimethyl-2,6,10,14-hexadecatetraen-1-ol diacetate Compound J: (Z,E,E)-7-hydroxymethyl-3,11,15-trimethyl-2,6,10,14-hexadecatetraen-1-ol Compound K: (E,Z,Z) & (E,E,Z)-7-hydroxymethyl-3,11,15-trimethyl-2,6,10,14-hexadecatetraen-1-ol Compound L: (E,E,E), (E,Z,E), (E,E,Z) & (E,Z,Z)-11-hydroxymethyl-3,7,15-trimethyl-2,6,10,14-hexadecatetraen-1-ol Compound M: (E,Z) & (E,E)-7-hydroxymethyl-3,11-dimethyl-2,6,10-dodecatrien-1-ol Compound N: (E,Z,E) & (E,E,E)-7,15-dihydroxymethyl-3,11-dimethyl-2,6,10,14-hexadecatetraen-1-ol Compound O: (E,E,E,E), (E,Z,E,E), (E,E,Z,E) & (E,Z,Z,E)-7-hydroxymethyl-3,11,15,19-tetramethyl-2,6,10,14,18-eicosapentaen-1-ol Compound P: (E,E,E,E), (E,Z,E,E), (E,E,Z,E) & (E,Z,Z,E)-7-hydroxymethyl-3,11,15,19-tetramethyl-2,6,10,14,18-eicosapentaen-1-ol diacetate Compound Q: (E,E,E,E), (E,Z,E,E), (E,E,Z,E) & (E,Z,Z,E)-7-hydroxymethyl-3,11,15,19-tetramethyl-2,6,10,14,18-eicosapentaen-1-ol dibenzoate (2) ANTI-STRESS ULCER ACTIVITY Test procedures The test was carried out in accordance with the method described by K. Takagi and S. Ckabe in *The Japanese Journal of Pharmacology*, vol. 18, 9 (1968), which is as follows:

Male rats (Donryu strain, body weight: 200-220 g) were placed under restraint in a stress cage and immersed vertically in the water bath kept at 2±1° C. to the height of the xiphoid of the animal. After restraint-immersion for 8 hours, the animals were sacrificed. The stomach was fixed with formalin and measured in its ulcer index[2]. The ulcer indices of the treated group and the control group were compared, and the inhibitory ratios were calculated. The test compound was orally administered for 3 days prior to and immediately before the restraint-immersion.

(2) ulcer index (mm): sum of the length of each linear ulcer

Test results

The anti-stress ulcer activity shown when the test compound was orally administered is set out in Table 2.

Table 2

| Test Compound | Dose (p.o. mg/kg/day × 4) | Number of rat | Ulcer index | Inhibitory ratio |
|---|---|---|---|---|
| Control | — | 16 | 22.3 | — |
| Compound A | 10 | 5 | 18.5 | 17 |
|  | 30 | 6 | 13.8 | 37* |
|  | 100 | 11 | 12.7 | 43* |
| Gefarnate | 100 | 5 | 25.3 | −13 |
|  | 300 | 11 | 35.0 | −57 |

*Significant inhibition at the probability of less than 0.05.

(3) Anti-cysteamine duodenal ulcer activity

Test procedures

The test was carried out in accordance with the method described by H. Selye and S. Szabo in Nature, vol. 244, 458 (1973), which is as follows.

Male rats (Donryu strain, body weight: 200–220 g) had been fasted overnight, were orally treated with 300 mg/kg of cysteamine to induce duodenal ulcer. The test compounds were orally administered four times, that is, for two days prior to, immediately before and on the day next to the treatment of cysteamine. The animals were killed two days after the treatment of cysteamine, and the duodenal ulcer index[3] was determined. The duodenal ulcer indices of the treated group and the control group were compared, and the inhibitory ratios were calculated.

[3] Duodenal ulcer index: Ulcer of each animal was scored according to the following criteria.

| | |
|---|---|
| 0: no lesion | |
| 1: hemorrhagic spots | |
| 2: product of longitudinal and latitudinal diameters (S)≦16 mm$^2$ | |
| 3: (S) ≦ 16 mm$^2$ | 16<(S) ≦ 25 |
| 4: (S) ≦ 16 mm$^2$ | (S) > 25 mm$^2$ |
| 5: perforated ulcer | |

Test results

The anti-cysteamine duodenal ulcer activity shown when the compound was orally administered is set out in Table 3.

Table 3

| Test Compound | Dose (p.o. mg/kg/day × 4) | No. of rat | Duodenal ulcer index | Inhibitory ratio |
|---|---|---|---|---|
| Control | — | 20 | 2.45 | — |
| Compound A | 100 | 10 | 2.00 | 18 |
|  | 300 | 18 | 1.56 | 34* |
| Gefarnate | 300 | 10 | 2.20 | 10 |
| L-Glutamine | 1000 | 10 | 1.70 | 31 |

*Significant inhibition at the probability of less than 0.05.

The acute toxicity of the compound A is set out in Table 4.

Table 4

| Tested animal | Dose of administration (orally given) | Death/Survival |
|---|---|---|
| ddY strain male mouse | 5,000 mg/kg | 0/5 |
| Donryu strain male rat | 1,000 mg/kg | 0/5 |

As seen from the Tables, the compounds of the aforementioned formula (I) are of value as medicines for treating peptic ulcer.

These compounds may be administered parenterally through subcutaneous or intramuscular injection, or orally in the form of tablets, capsules, granules, powders and the like. The dosage to be administered may vary depending upon condition, age, weight, administration procedure and the like, and a dosage of about 10–1000 mg per day is usually given to an adult at once or in the form of 2–4 divided portions.

The representatives of the compounds having the aforementioned formula (I) are set out below. However, these examples are not meant to limit the compounds of the present invention.

(1)  7-Hydroxymethyl-3,11-dimethyl-2,6,10-dodecatrien-1-ol, and its diacetate and dibenzoate (2)  7-Hydroxymethyl-3,11,15-trimethyl-2,6,10,14-hexadecatetraen-1-ol, and its diacetate, dicaproate, dilaurate, dipalmitate, dicrotonate, dibenzoate, bis-p-methylbenzoate, bis-p-methoxybenzoate, bis-p-chlorobenzoate, bisphenylacetate and dicinnamate (3)  7-Hydroxymethyl-3,11,15-trimethyl-2,6,10,14-hexadecatetraen-1-ol dimethyl ether (4)  11-Hydroxymethyl-3,7,15-trimethyl-2,6,10,14-hexadecatetraen-1-ol, and its diacetate and dibenzoate (5)  7,15-Dihydroxymethyl-3,11-dimethyl-2,6,10,14-hexadecatetraen-1-ol, and its triacetate and tribenzoate (6)  7-Hydroxymethyl-3,11,15,19-tetramethyl-2,6,10,14,18-eicosapentaen-1-ol, and its diacetate and dibenzoate (7)  7-Hydroxymethyl-3,11,15,19,23-pentamethyl-2,6,10,14,18,22-tetracoashexaen-1-ol, and its diacetate and dibenzoate The above exemplified compounds are present as a number of isomers due to configuration of the double bonds. Therefore, the above exemplified compounds may be obtained in the form of a number of isomers set out below and mixtures of these isomers.

Compound (1): (E,Z) and (E,E) isomers

Compounds (2) and (3): (E,Z,E), (E,E,E), (Z,E,E), (Z,Z,E), (Z,Z,Z), (Z,E,Z), (E,Z,Z) and (E,E,Z) isomers Compound (4): (E,E,E), (E,Z,E), (E,E,Z), (Z,E,E), (Z,Z,E), (Z,Z,Z), (Z,E,Z) and (E,Z,Z) isomers Compound (5): (E,Z,E,E), (Z,E,E,E), (Z,Z,E,E), (E,Z,Z,E), (E,E,Z,E), (Z,Z,Z,E), (Z,E,Z,E) and (E,E,E,E) isomers Compound (6): (E,E,E,E), (E,Z,E,E), (E,E,Z,E), (Z,E,E,E), (Z,Z,E,E), (Z,E,Z,E), (Z,Z,Z,E) and (E,Z,Z,E) isomers Compound (7): (E,E,E,E,E), (E,Z,E,E,E), (E,E,Z,E,E), (Z,E,E,E,E), (Z,Z,E,E,E), (Z,E,Z,E,E), (Z,Z,Z,E,E) and (E,Z,Z,E,E) isomers According to the present invention, the compounds of the aforementioned formula (I) can be obtained by the following processes.

Process I (E,Z,E)-7-Hydroxymethyl-3,11,15-trimethyl-2,6,10,14-hexadecatetraen-1-ol, one of the compounds having the aforementioned formula (I) can be obtained by extracting a plant belonging to the genus Croton and isolating the desired compound from the extract.

The plant material to be subjected to the extraction may be crude drugs originating from plants belonging to the genus Croton growing in Thailand, the plants being exemplified by Plau-noi (*Croton columnaris* Airy Shans, another name; *Croton joufra* Roxb.), Plau-luat (*Croton hutchinsonianus* Hosseus) and Plau-yai (*Croton oblongifolius* Roxb.). Palu-noi is preferred.

There is no specific limitation on the solvent employed for the above-mentioned extraction, so far as it belongs to the solvent ordinarily employed for extraction of plant ingredients. Preferred examples of the solvent are water; an alcohol such as methanol and ethanol; an ether such as ethyl ether and isopropyl ether; a halogenated hydrocarbon such as methylene chloride and chloroform; an acetic acid ester such as methyl acetate and ethyl acetate; a lower alkyl ketone such as acetone and methyl ethyl ketone; and an aromatic hydrocarbon such as benzene and toluene.

Isolation of the above-named compound from the extract can be carried out by employing the usual procedure for recovering neutral ingredients. In addition to that procedure, either column chromatography or crystallization of its derivative may preferably be adopted to isolate the desired compound.

The procedures may be illustrated as follows: The extract obtained as stated above or its aqueous suspension is washed with a hydrocarbon such as n-hexane to remove the lipid, and extracted with a water-immiscible solvent such as benzene and ether. The so obtained organic layer is washed with an aqueous solution containing an alkali hydrogencarbonate such as sodium hydrogen-carbonate and potassium hydrogencarbonate, an alkali carbonate such as sodium carbonate and potassium carbonate, or an alkali hydroxide such as sodium hydroxide and potassium hydroxide, to remove the acidic materials. The organic solution thus obtained is charged on a column consisting of, for instance, silica gel, alumina or silicic acid and eluted with an organic solvent, for instance, ethyl ether, benzene, chloroform, ethyl acetate and acetone, mixtures of these solvents, and mixtures between these solvents and petroleum solvents such as n-pentane and n-hexane. The desired compound having the above-mentioned name can be obtained by evaporating the solvent from the eluate.

The desired compound obtained above can be, if necessary, further purified by the conventional method such as production of its derivative or distillation under reduced pressure. According to the method for purification through preparation of derivatives, the neutral ingredient obtained from the plant extract is treated with a reagent commonly employed for production of crystalline derivatives of alcohols such as 3,5-dinitrobenzoyl chloride, phenyl isocyanate and phthalic anhydride to recover the crystalline derivative. The derivative thus obtained is then hydrolyzed to give the pure desired compound.

Process II

A compound having the aforementioned formula (I) having the 6Z-configuration and the 7-hydroxymethyl group, namely, a compound having the formula

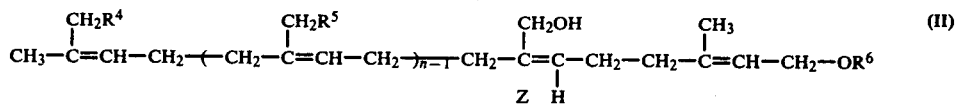

in which $R^4$ and $R^5$ may be the same or different and each represents hydrogen atom, hydroxyl group or an alkoxy group having 1-8 carbon atoms, $R^6$ represents hydrogen atom or an alkyl group having 1-8 carbon atoms, and n is an integer of 1-4, can be obtained by reacting a compound having the formula

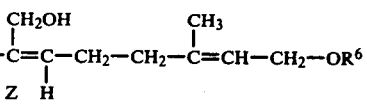

in which $R^7$ and $R^8$ may be the same or different and each represents hydrogen atom, a protected hydroxyl group or an alkoxy group having 1-8 carbon atoms, $R^{10}$ represents a hydrocarbon residue such as phenyl and n-butyl, X represents a halogen atom such as bromine and iodine, and n is an integer of 1-4 and a compound having the formula $$OHC-CH_2-CH_2-\overset{CH_3}{\underset{|}{C}}=CH-CH_2-OR^9 \qquad (IV)$$

in which $R^9$ represents a protecting group for the hydroxyl group or an alkyl group having 1-8 carbon atoms with paraformaldehyde in the presence of a base, and removing the protecting group of the hydroxyl group of the resulting compound having the formula (V)

$$CH_3-\overset{CH_2R^7}{\underset{|}{C}}=CH-CH_2+CH_2-\overset{CH_2R^8}{\underset{|}{C}}=CH-CH_2\overline{)_{n-1}}CH_2-\overset{CH_2OH}{\underset{\underset{H}{Z}}{C}}=\overset{}{C}-CH_2.CH_2-\overset{CH_3}{\underset{|}{C}}=CH-CH_2-OR^9$$

in which $R^7$, $R^8$, $R^9$ and n have the same meanings as defined hereinbefore.

There is no specific limitation on the protecting group for the hydroxyl group, so far as it does not affect other moieties of the compound when the said protecting group is converted to the free hydroxyl group. This protecting group is exemplified by 5 or 6-membered cyclic group containing oxygen or sulfur in the ring which may be substituted with alkoxy, such as 2-tetrahydrofuranyl, 2-tetrahydropyranyl, 2-tetrahydrothienyl, 2-tetrahydrothiopyranyl and 4-methoxytetrahydropyran-4-yl, an alkoxy-(lower)alkyl group such as methoxymethyl, ethoxymethyl, n-propoxymethyl, isopropoxymethyl, n-butoxymethyl, isobutoxymethyl, 1-ethoxyethyl, 1-ethoxypropyl and 1-methoxy-1-methylethyl, and tri(lower)alkylsilyl group such as trimethylsilyl, triethylsilyl, tri-n-propylsilyl, triisopropylsilyl, tri-n-butylsilyl and triisobutylsilyl. Particularly, 2-tetrahydropyranyl, methoxymethyl, 1-ethoxyetbyl, 1-methoxy-1-methylethyl and trimethylsilyl are preferred. However, these examples are not limitative.

In the present process, the reaction involving the compound of the formula (III), the compound of the formula (IV) and paraformaldehyde for preparing the compound of the formula (V) is carried out in the presence of a base and a solvent. There is no specific limitation on the base employed, so far as it belongs to the base adopted for the general Wittig reaction. Preferred is an alkyllithium such as n-butyllithium, sec-butyllithium, and tert-butyllithium. There likewise is no specific limitation on the solvent employed, so far as it does not participate in the reaction. Preferred are an ether such as ethyl ether, tetrahydrofuran, dioxane and 1,2-dimethoxyethane and an aliphatic hydrocarbon such as n-pentane and n-hexane. The reaction temperature preferably is a relatively low temperature and most preferably is between $-80°$ C. and room temperature. Further, the reaction is preferably carried out in a stream of an inert gas such as nitrogen, helium and argon. Most preferred procedure for this reaction is as follows. The compound of the general formula (III) is dissolved in an organic solvent such as tetrahydrofuran, and to this solution is added a base such as n-butyllithium at $-5°$-$0°$ C. in a stream of an inert gas such as argon. Subsequently, the compound of the general formula (IV) is added around $-78°$ C., sec-butyllithium or tert-butyllithium is added around $-50°$ C., and paraformaldehyde is added between $-10°$ C. and room temperature, whereby the reaction proceeds. The reaction period of time varies depending mainly upon kind of the base employed and the reaction temperature. Ordinarily, the period is between 2 and 6 hours.

After completion of the reaction, the desired compound of the aforementioned general formula (V) can be recovered from the reaction mixture in the conventional manner. For instance, after completion of the reaction, the reaction mixture is added to ice-water and extracted with an organic solvent such as n-hexane. The organic solvent layer is washed and dried. Upon evaporation of the solvent, the desired compound is obtained. The desired compound thus obtained can, if necessary, be further purified by the conventional method such as column chromatography and thin layer chromatography.

The reaction for the preparation of the compound of the aforementioned formula (II) which involves removing the protecting group of the hydroxyl group from the compound of the aforementioned formula (V) may be chosen depending upon kind of the protecting group. In case, for instance, the protecting group for the hydroxyl is a heterocyclic group such as 2-tetrahydropyranyl or an alkoxyalkyl group such as methoxymethyl, the reaction is easily carried out by bringing the compound (V) into contact with an acid. Preferred acids are an organic acid such as formic acid, acetic acid, propionic acid and p-toluenesulfonic acid and an inorganic acid such as hydrochloric acid and sulfuric acid. The reaction is carried out in the presence or absence of a solvent. However, a solvent is preferably employed so as to carry out the reaction smoothly. Preferred solvents are water, an alcohol such as methanol and ethanol, and a mixture of water and one of these alcohols. There is no specific limitation on the reaction temperature, but room temperature is preferably adopted. In case the protecting group for the hydroxyl group is a trialkylsilyl group such as trimethylsilyl, the reaction is easily carried out by bringing the compound (V) into contact with water or an aqueous solution of an acid or a base. As the acid and base, there may be mentioned an acid such as an organic acid, e.g., formic acid, acetic acid and propionic acid, and an inorganic acid, e.g., hydrochloric acid and sulfuric acid, a base such as hydroxide of an alkali metal and an alkaline earth metal, e.g., potassium hydroxide and calcium hydroxide, and carbonate of an alkali metal and an alkaline earth metal, e.g., potassium carbonate and calcium carbonate. There is no specific limitation on the reaction temperature, but, in general, room temperature is preferably adopted. The period of time required for removing the protecting group varies depending upon kind of the protecting group.

After completion of the reaction, the desired compound of the formula (II) can be obtained from the reaction mixture in the conventional manner. For instance, the reaction mixture is, after completion of the reaction, neutralized and extracted with an organic solvent such as ethyl ether. The organic solvent layer is washed and dried. Upon evaporation of the solvent, the desired compound is obtained. The desired compound thus obtained can, if necessary, be further purified by the conventional method such as column chromatography and thin layer chromatography.

Process III

A compound having the aforementioned formula (I) which is a mixture of the Z and E isomers at the 6-position, namely, a compound having the formula

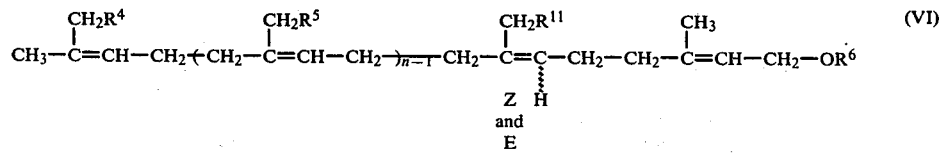

in which $R^4$, $R^5$, $R^6$ and n have the same meanings as defined hereinbefore, and $R^{11}$ represents hydrogen atom, hydroxyl group or an alkyl group having 1-8 carbon atoms can be obtained by reacting a compound having the formula

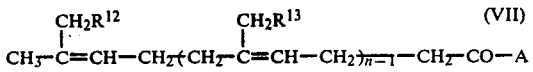
(VII)

in which $R^{12}$ and $R^{13}$ may be the same or different and each represents hydrogen atom, a protected hydroxyl group or an alkoxy group having 1-8 carbon atoms, A represents methyl group, a protected hydroxymethyl group, a protected formyl group or an alkoxymethyl group having 1-8 carbon atoms, and n has the same meaning as defined hereinbefore
with a compound having the formula

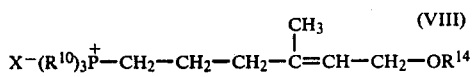
(VIII)

in which $R^{10}$ and X have the same meanings as defined hereinbefore, and $R^{14}$ represents a protecting group for the hydroxyl group or an alkyl group having 1-8 carbon atoms
in the presence of a base to prepare a compound having the formula

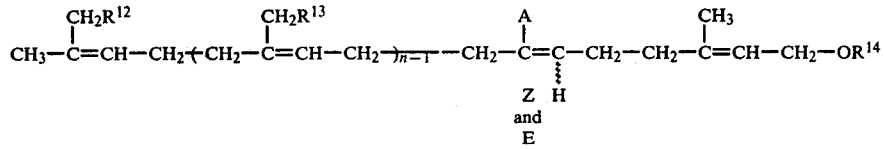
(IX)

in which $R^{12}$, $R^{13}$, $R^{14}$, A and n have the same meanings as defined hereinbefore, removing the protecting groups of the hydroxyl group and/or the formyl group and, if desired, reducing the compound thus obtained.

The protecting group for the hydroxyl group may be the same as exemplified in Process I. In addition, the said protecting group may be an aliphatic or aromatic acyl group such as acetyl, propionyl, butyryl, isobutyryl and benzoyl. Particularly preferred are 2-tetrahydropyranyl, methoxymethyl, trimethylsilyl, acetyl and benzoyl groups.

There is no specific limitation on the protecting group for the formyl group, so far as it belongs to the group capable of forming a usual acetal. Preferred are groups which form dimethoxymethyl, diethoxymethyl and ethylenedioxymethyl groups.

In the present process, the condensation reaction involving the compound of the formula (VII) and the compound of the formula (VIII) for preparing the compound of the formula (IX) is carried out in the presence of a base and a solvent. There is no specific limitation on the base employed, so far as it belongs to the base adopted for the general Wittig reaction. Preferred are an alkyllithium such as n-butyllithium, sec-butyllithium and tert-butyllithium, a lithium dialkylamide such as lithium diethylamide and lithium diisopropylamide, an alkali metal hydride such as sodium hydride, an alkali metal amide such as sodium amide and potassium amide, and an alkali metal alcoholate such as potassium tert-butoxide. There likewise is no specific limitation on the solvent employed, so far as it does not participate in the reaction. Preferred are an ether such as ethyl ether, tetrahydrofuran, dioxane and 1,2-dimethoxyethane, an aliphatic hydrocarbon such as n-pentane and n-hexane, an aromatic hydrocarbon such as benzene and toluene, a dialkylaliphatic acid amide such as dimethylformamide and dimethylacetamide, and dimethylsulfoxide.

There is no specific limitation on the reaction temperature. However, a relatively low temperature is preferably adopted so as to avoid the side-reactions. Most preferably, the reaction is carried out at a temperature between $-20°$ C. and room temperature and in a stream of an inert gas such as nitrogen, helium and argon. Most preferred procedure for this reaction is as follows. The compound of the formula (VIII) is dissolved in an organic solvent such as tetrahydrofuran, and to this solution is added a base such as n-butyllithium and sodium hydride at $-20°$-$0°$ C. in a stream of an inert gas such as argon. Subsequently, the compound of the formula (VII) is added below room temperature whereby the reaction proceeds. The reaction period of time varies depending mainly upon kind of the base employed and the reaction temperature. Ordinarily, the period is between 2 and 8 hours.

After completion of the reaction, the desired compound of the formula (IX) can be recovered from the reaction mixture in the conventional manner. For instance, after completion of the reaction, ice-water is added to the reaction mixture and this is extracted with an organic solvent such as n-hexane. The organic solvent layer is washed and dried. Upon evaporation of the solvent, the desired compound is obtained. The desired compound thus obtained can, if necessary, be further purified by the conventional method such as column chromatography and thin layer chromatography.

The reaction for removing the protecting group of the hydroxyl group from the compound having the formula (IX) may be chosen depending upon kind of the protecting group to be removed. In case, for instance, the protecting group for the hydroxyl group is an acyl group such as acetyl and benzoyl, the reaction is carried out by employing usual processes for hydrolyzing or alcoholyzing an ester group with a base or an acid. Preferred is a process involving bringing the compound (IX) into contact with a base. Preferred bases are hydroxides of an alkali metal and alkaline earth metal such as sodium hydroxide, potassium hydroxide and barium hydroxide, and carbonates of an alkali metal and an alkaline earth metal such as sodium carbonate, potassium carbonate and calcium carbonate. The present reaction is preferably carried out in water, an organic solvent such as an alcohol, e.g., methanol, ethanol and n-propanol, an ether e.g., tetrahydrofuran and dioxane, or a mixture of water and one of the said organic solvents. There is no specific limitation on the reaction temperature, but, in general, temperatures around room temperature are preferably adopted. The reaction for removing the hydroxyl protecting group other than the above can be conducted under the same conditions as described in the Process II wherein the compound (II) is prepared from the compound (V).

The reaction for removing the protecting group from the formyl group of the compound having the formula (IX) wherein the substitute A is a protected formyl group can be performed in the manner as employed for hydrolysis of the usual acetal. Preferred is a method that involves bringing the compound (IX) into contact with an acid. As a preferred acid to be used, there may be mentioned an organic acid such as formic acid, acetic acid and propionic acid and an inorganic acid such as hydrochloric acid and sulfuric acid. The present reaction is carried out in water or an aqueous organic solvent. Preferred aqueous organic solvent are an aqueous alcohol such as aqueous methanol and aqueous ethanol and an aqueous ether such as aqueous tetrahydrofuran and aqueous dioxane. There is no specific limitation on the reaction temperature, but, in general, temperatures around room temperature are preferably adopted.

After completion of the reaction, the compound obtained by removal of the protecting group of the formyl group can be recovered from the reaction mixture in the conventional manner. For instance, after completion of the reaction, the reaction mixture is extracted with an organic solvent such as n-hexane. The organic solvent layer is washed and dried. Upon evaporation of the solvent, the desired compound is obtained. Reduction of the compound carrying formyl group which is obtained above is preformed by bringing the said compound into contact with a reducing agent in the presence of a solvent. There is no specific limitation on the reducing agent employed, so far as it is capable of reducing only formyl group into hydroxymethyl group without affecting other moieties of the compound. Preferred are an alkali metal hydride complex salt such as sodium borohydride, lithium aluminum hydride and potassium borohydride, and aluminum triisopropoxide. There likewise is no specific limitation on the solvent employed, so far as it does not participate in the reaction. In the case of using the alkali metal hydride complex salt, an alcohol as methanol and ethanol and an ether such as ethyl ether, tetrahydrofuran and dioxane are preferred. In the case of using the aluminum tri-iso-propoxide, isopropanol may be employed. There is no specific limitation on the reaction temperature, but temperatures between 0° C. and room temperature are preferably adopted.

After completion of the reaction, the desired compound is recovered from the reaction mixture in the conventional manner. For instance, after completion of the reaction, excess reagent is decomposed and extracted with an organic solvent such as n-hexane. The extract is washed and dried. Upon evaporation of the solvent, the desired compound is obtained.

In case the compound obtained by the reduction carries a remaining protecting group for the hydroxyl group, the desired compound of the aforementioned formula (VI) can be obtained by removal of the remaining protecting group in the manner mentioned above. The desired compound thus obtained can, if necessary, be further purified by the conventional method such as column chromatography and thin layer chromatography.

Process IV

A compound having the aforementioned formula (I) which is a mixture of the Z and E isomers at the 6-position and hydroxymethyl group is present at the 7-position, namely, a compound having the formula

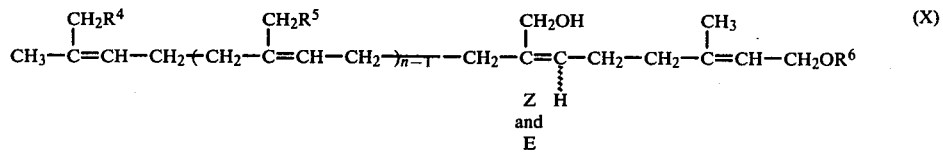

in which $R^4$, $R^5$, $R^6$ and n have the same meanings as defined hereinbefore
can be obtained by reacting a compound having the formula

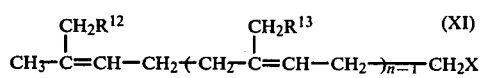

in which $R^{12}$, $R^{13}$, X and n have the same meanings as defined hereinbefore
and a compound having the formula $$(R^{16}O)_2POCH_2COOR^{15} \qquad (XII)$$

in which $R^{15}$ and $R^{16}$ may be the same or different and each represents an alkyl group having 1–4 carbon atoms
with a compound having the formula

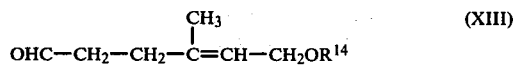

in which $R^{14}$ has the same meaning as defined hereinbefore
in the presence of a base to prepare a compound having the formula

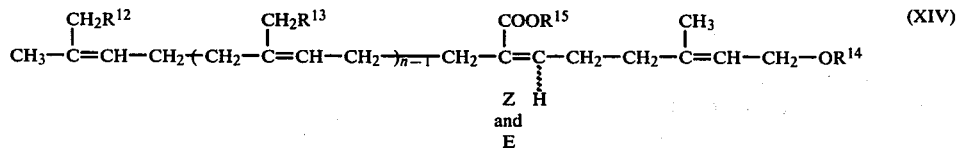

in which $R^{12}$, $R^{13}$, $R^{14}$, $R^{15}$ and n have the same meanings as defined hereinbefore,
and subjecting the above obtained compound to reduction and removal of the protecting group.

In the present process, the condensation reaction involving the compound of the formula (XI), the compound of the formula (XII) and the compound of the formula (XIII) for preparing the compound of the formula (XIV) is carried out in the presence of a base and a solvent. There is no specific limitation on the base employed, so far as it belongs to the base adopted for the modified Wittig reaction [W. S. Wadsworth and W. D. Emmons, J. Am. Chem. Soc., Vol. 83, 1733 (1961)].

Preferred are an alkyllithium such as n-butyllithium and tert-butyllithium, a hydride of an alkali metal or an alkaline earth metal such as sodium hydride and calcium hydride, an alkali metal amide such as sodium amide and potassium amide, and an alkali metal alcoholate such as sodium methoxide, sodium ethoxide, potassium ethoxide and potassium tert-butoxide. There is no specific limitation on the solvent employed, so far as it does not participate in the reaction. Preferred are an ether such as ethyl ether, tetrahydrofuran and 1,2-dimethoxyethane, an aliphatic hydrocarbon such as n-pentane and n-hexane, a halogenated hydrocarbon such as methylene chloride, chloroform and ethylene dichloride, an aromatic hydrocarbon such as benzene and toluene, an aliphatic alcohol such as methanol, ethanol, n-propanol, isopropanol and tert-butanol, a dialkyl aliphatic acid amide such as dimethylformamide and diethylformamide, and dimethylsulfoxide. An appropriate solvent is chosen, in view of the base employed. There likewise is no specific limitation on the reaction temperature. Preferably the reaction is conducted at approximately 0°–70° C. in a stream of an inert gas such as nitrogen, helium and argon. The most preferable procedure is as follows. The compound of the formula (XII) is dissolved in an organic solvent such as 1,2-dimethoxyethane, and, in a stream of an inert gas such as argon, to this solution is added at a temperature between 0° C. and room temperature a base and then added the compound of the formula (XI) at a temperature between room temperature and 50° C. Subsequently, the above-mentioned base is again added around 0° C., and the compound of the formula (XIII) is then added at a temperature between room temperature and 50° C. The reaction period of time may vary depending mainly upon kind of the base employed and the reaction temperature. Ordinarily, the period is between 2 and 5 hours.

After completion of the reaction, the desired compound of the formula (XIV) can be recovered from the reaction mixture in the conventional manner. For instance, after completion of the reaction, ice-water is added to the reaction mixture and this is extracted with an organic solvent such as n-hexane. The organic solvent layer is washed and dried. Upon evaporation of the solvent, the desired compound is obtained. The desired compound thus obtained can, if necessary, be further purified by the conventional method such as column chromatography and thin layer chromatography.

The reaction for reducing the so obtained compound of the formula (XIV) is carried out by bringing the said compound into contact with a reducing agent in the presence of a solvent. There is no specific limitation on the reducing agent employed, so far as it is capable of reducing an ester group only into hydroxymethyl group without affecting other moieties of the compound. Preferred is an aluminum hydride compound such as aluminum hydride, lithium aluminum monoethoxyhydride, diisobutylaluminum hydride and sodium bis-(2-methoxyethoxy)aluminum hydride. Preferred solvents employed are an ether such as ethyl ether and tetrahydrofuran, an aliphatic hydrocarbon such as n-pentane and n-hexane, and an aromatic hydrocarbon such as benzene and toluene. There is no specific limitation on the reaction temperature, but temperatures between −10° C. and room temperature are preferably adopted.

The reaction for removing the protecting group of the hydroxyl group of the compound having the formula (XIV) can be carried out in the manner as described hereinbefore. However, where the protecting group for the hydroxyl group is an acyl group such as acetyl and benzoyl, the said protecting group can conveniently be removed during the above-mentioned reduction.

After completion of the reaction, the desired compound of the formula (X) which is obtained through the reduction and the removal of the protecting group of the hydroxyl group can be recovered from the reaction mixture in the conventional manner. For instance, after completion of the reaction, ethyl acetate is added to the reaction mixture to decompose an excess of the reducing agent, and the resulting precipitate is then filtered off. Upon evaporation of the solvent from the filtrate, the desired compound is obtained. The desired compound thus obtained can, if necessary, be further purified by the conventional method such as column chromatography and thin layer chromatography.

Process V

A compound having the aforementioned formula (I) wherein the configuration at the 6-position is E and hydroxymethyl group is present at the 7-position, namely, a compound having the formula

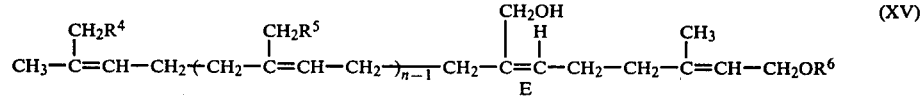
(XV)

in which $R^4$, $R^5$, $R^6$ and n have the same meanings as defined hereinbefore
can be obtained by isomerization of a compound having the formula

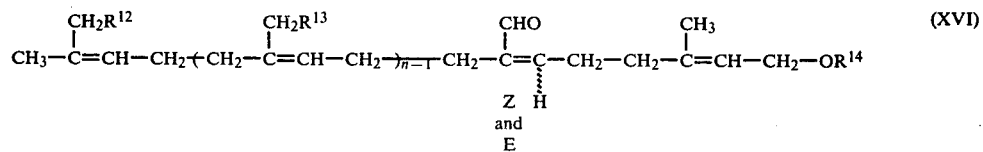
(XVI)

in which $R^{12}$, $R^{13}$, $R^{14}$ and n have the same meanings as defined hereinbefore
to prepare a compound having the formula

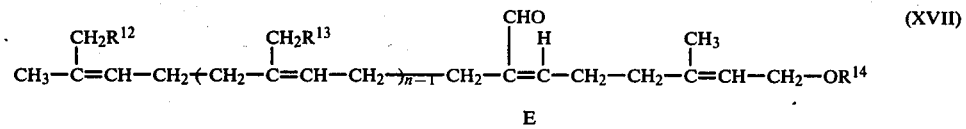

in which $R^{12}$, $R^{13}$, $R^{14}$ and n have the same meanings as defined hereinbefore,
and subjecting the above-obtained compound to removal of the protecting group of the hydroxyl group and reduction.

In the present process, the reaction involving isomerization of the compound of the formula (XVI) to prepare the compound of the formula (XVII) is carried out by using a catalyst in the presence or absence of a solvent. There is no specific limitation on the catalyst employed, so far as it belongs to the catalyst which may be used for isomerization of double bonds. Preferred are a base; for instance, an alkali metal hydroxide such as sodium hydroxide and potassium hydroxide and an alkali metal alcoholate such as sodium methoxide, sodium ethoxide and potassium tert-butoxide; an inorganic acid such as hydrochloric acid, sulfuric acid and perchloric acid; an organic acid such as benzenesulfonic acid and p-toluenesulfonic acid; a Lewis acid such as boron fluoride and aluminum chloride; iodine; palladium metal; and a radical-reaction initiating agent such as 2,2'-azobisisobutyronitrile and benzoyl peroxide. There is no specific limitation on the solvent which is optionally used, so far as it does not participate in the reaction. Preferred are water, an organic solvent, for instance, an alcohol such as methanol, ethanol and n-propanol, an ether such as ethyl ether, tetrahydrofuran and dioxane and an aromatic hydrocarbon such as benzene and toluene, and a mixture of water and one of these organic solvents. There likewise is no specific limitation on the reaction temperature, but temperatures between room temperature and the reflux temperature of the solvent used are preferably adopted. The reaction period of time may vary depending mainly upon kind of the catalyst and the reaction temperature. Ordinarily, the period is between 2 and 12 hours.

After completion of the reaction, the desired compound of the formula (XVII) can be recovered from the reaction mixture in the conventional manner. For instance, after completion of the reaction, the desired compound can be obtained by the following procedures, after neutralization of the reaction mixture if necessary. After evaporation of the solvent, the reaction mixture is extracted with an organic solvent such as ethyl ether. The organic solvent layer is washed and dried. Upon evaporation of the solvent from the extract, the desired compound is obtained.

The reaction for removing the protecting group of the hydroxyl group of the compound having the formula (XVII) and the reaction for reducing the said compound are both carried out in the manner mentioned hereinbefore. However, the said protecting group may be removed during the isomerization or the reduction.

The desired compound of the formula (XV) which is obtained above may be further purified, if necessary, by the conventional method such as column chromatography and thin layer chromatography.

Process VI

A compound having the formula (I) wherein each of $R^1$ and $R^2$ represents the acyloxy group defined hereinbefore and $R^3$ represents the acyl group defined hereinbefore can be obtained by acylating the hydroxyl group of one of the compounds prepared in the aforementioned Processes I to V.

In the present process, the reaction may be performed by bringing the compound carrying hydroxyl groups into contact with an acylating agent in the presence or absence of a solvent. There is no specific limitation on the acylating agent employed, so far as it belongs to one which is generally used for acylating a hydroxyl group. Preferred are an acid anhydride such as acetic anhydride, propionic anhydride and caproic anhydride, and an acid chloride such as acetyl chloride, acetyl bromide, butyryl chloride, isobutyryl chloride, octanoyl chloride, lauroyl chloride, palmitoyl chloride, crotonoyl chloride, benzoyl chloride, p-methoxybenzoyl chloride, phenylacetyl chloride and cinnamoyl chloride. The present reaction is preferably carried out in the presence of a base. Such a base is exemplified by an organic base such as triethylamine, pyridine, picoline and lutidine, an inorganic base, for instance, an alkali metal hydroxide such as sodium hydroxide and potassium hydroxide and an alkali metal carbonate such as sodium carbonate and potassium carbonate, and an alkali metal salt of an organic acid such as sodium acetate and potassium acetate. There is no specific limitation on the solvent which is optionally employed, so far as it does not participate in the reaction. Preferred are water, an ether such as ethyl ether, tetrahydrofuran and dioxane, a halogenated hydrocarbon such as methylene chloride and chloroform, an aromatic hydrocarbon such as benzene and toluene and a heterocyclic base such as pyridine and picoline. There likewise is no specific limitation on the reaction temperature, but temperatures between 0° C. and room temperature are preferably adopted. The reaction period of time may vary depending mainly upon kind of the acylating agent and the reaction temperature. The period ordinarily is between 2 and 10 hours.

After completion of the reaction, the desired compound can be recovered from the reaction mixture in the conventional manner. For instance, after completion of the reaction, the reaction mixture is added to ice-water and extracted with an organic solvent such as ethyl ether. The organic solvent layer is washed and dried. Upon evaporation of the solvent from the extract, the desired compound is obtained. The desired compound thus obtained can be further purified, if necessary, by the conventional method such as column chromatography and thin layer chromatography.

Process VII

A compound having the formula (I) wherein each of $R^1$ and $R^2$ represents the alkoxy group as defined hereinbefore and $R^3$ represents the alkyl group as defined hereinbefore can be obtained by alkylating the hydroxyl group of one of the compounds prepared in the aforementioned Processes I to V.

In the present process, the reaction may be performed by bringing the compound carrying hydroxy groups into contact with an alkylating agent in the presence or absence of a solvent. There is no specific limitation on the alkylating agent employed, so far as it belongs to one which is generally used for alkylating a hydroxyl group. Preferred are an alkyl halide and a dehydrohalogenating agent. The alkyl halide is exemplified by methyl chloride, methyl bromide, methyl iodide, ethyl iodide, n-propyl iodide, isopropyl iodide, n-butyl iodide, isobutyl iodide, hexyl iodide and octyl iodide. The dehydrohalogenating agent is exemplified by a metal oxide such as silver oxide, calcium oxide and barium oxide, a metal hydride such as sodium hydride and calcium hydride and a metal amide such as sodium amide and potassium amide. There is no specific limitation on the solvent which is optionally employed, so far as it does not participate in the reaction. Preferred are an ether such as tetrahydrofuran and dioxane, an aromatic hydrocarbon such as benzene and toluene, a dialkyl aliphatic acid amide such as dimethylformamide and dimethylacetamide, and dimethylsulfoxide. There likewise is no specific limitation on the reaction temperature, but temperatures around room temperature are preferably adopted. The reaction period of time varies depending mainly upon kind of the alkylating agent and the like. The period ordinarily is between 5 and 20 hours.

After completion of the reaction, the desired compound can be recovered from the reaction mixture in the conventional manner. For instance, after completion of the reaction, an excess of the alkyl halide is removed from the reaction mixture by evaporation. Water is added to the residue, and the resulting mixture is extracted with an organic solvent such as n-hexane. The organic solvent layer is washed and dried. Upon evaporation of the solvent, the desired compound is obtained. The desired compound thus obtained can be

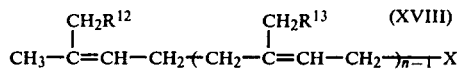

in which $R^{12}$, $R^{13}$, X and n have the same meanings as defined hereinbefore
with a compound having the formula

in which A represents an alkoxymethyl group having 1–8 carbon atoms or a protected formyl group such as dimethoxymethyl, diethoxymethyl and ethylenedioxymethyl and $R^{17}$ represents an alkyl group having 1–4 carbon atoms
in the presence of a base, and subjecting the resulting compound to hydrolysis and decarboxylation.

The present reaction is carried out in the presence of a base and a solvent. There is no specific limitation on the base employed, so far as it belongs to the base which is generally used for alkylating an active methylene group. Preferred are an alkali metal alcoholate such as sodium methoxide, sodium ethoxide and potassium tert-butoxide, hydrides of an alkali metal and an alkaline earth metal such as sodium hydride and calcium hydride, and an alkyllithium such as n-butyllithium, sec-butyllithium and tert-butyllithium.

Hydrolysis and decarboxylation of the above-obtained compound are carried out under the same conditions as employed in the general ketonic hydrolysis of a β-ketoester. Preferably, the reaction is conducted by heating under reflux the said compound with an alkali metal hydroxide such as sodium hydroxide and potassium hydroxide in an aqueous alcohol such as aqueous methanol and aqueous ethanol.

(2) A compound having the formula (VII) in which A represents an acyloxymethyl group that is one of a protected hydroxymethyl group can be prepared by the following steps.

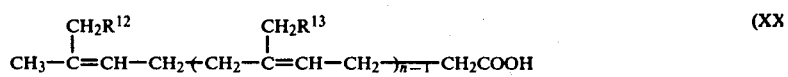

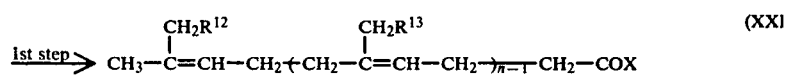

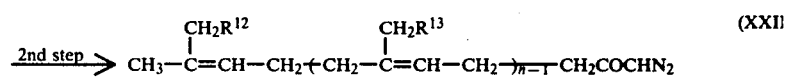

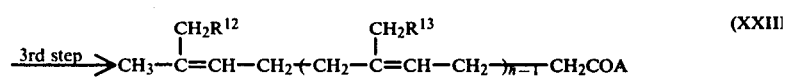

further purified, if necessary, by the conventional method such as column chromatography and thin layer chromatography.

The compound of the formula (VII) which is employed as the starting compound in the aforementioned Process III is a novel compound with exception of geranylacetone and can be prepared by, for instance, the processes stated below.

(1) A compound having the formula (VII) in which A represents an alkoxymethyl group or a protected formyl group can be prepared by reacting a compound having the general formula In the above formulae, $R^{12}$, $R^{13}$, X and n have the same meaning as defined hereinbefore, and A represents an acyloxymethyl group such as acetyloxymethyl and propionyloxymethyl that is one of a protected hydroxymethyl group.

The first step is directed to the preparation of the carboxylic acid halide derivative of the formula (XXI) and performed by reacting carboxylic acid derivative with a halogenating agent in the presence or absence of a solvent. There is no specific limitation on the halogenating agent, so far as it belongs to one which is generally used for preparation of an acid halide. Preferred halogenating agents are thionyl chloride, thionyl bromide, phosphorus trichloride, phosphorus tribromide and oxalyl chloride.

The second step is directed to the preparation of the diazoketone of the formula (XXII) and performed by reacting acid halide of the formula (XXI) with diazomethane in the presence of a solvent.

The third step is directed to the preparation of the compound of the formula (XXIII) wherein A represents an acyloxymethyl group and performed by heating a diazoketone of the formula (XXII) with a carboxylic acid such as acetic acid and propionic acid.

The present invention will be further concretely illustrated by the following examples and referential examples.

EXAMPLE 1

(E,Z,E)-7-Hydroxymethyl-3,11,15-trimethyl-2,6,10,14-hexadecatetraen-1-ol (1) Process utilizing extraction of a plant A crushed crude drug of Plau-noi growing in Thailand (28 kg) was extracted with three portions of 20 l. of methanol under reflux. The extracts were combined and evaporated to remove the solvent to obtain 672 g of a residue. This residue was dissolved in 5 l. of 90% methanol and washed with n-hexane. The methanol was evaporated to leave a residue which was then suspended in 3 l. of water and extracted with ether. The ethereal layer was washed with an aqueous sodium carbonate solution (5%) and dried over anhydrous sodium sulfate. The solvent was then evaporated to dryness, leaving 117 g of an oil. The so obtained oil was charged on the silica gel (1.5 kg) column. Elution was effected first with benzene containing 10% ethyl acetate and then with benzene containing 30% ethyl acetate. The eluate portions containing the desired ingredient were chosen from the eluates which were eluted with benzene containing 30% ethyl acetate, and the solvent was evaporated to dryness, leaving 17 g of the desired product.

(2) Process utilizing synthetic steps

In 60 ml of anhydrous tetrahydrofuran was suspended 9.0 g of (E)-5,9-dimethyl-4,8-decadien-1-yltriphenylphosphonium iodide [R. M. Coates and W. H. Robinson, J. Am. Chem. Soc., 93, 1785 (1971)]. To this suspension was added dropwise the equimolar amount of a n-butyllithium-hexane solution at −5°-0° C. in a stream of argon. After stirring for 30 minutes at room temperature, the reaction mixture was cooled to −78° C., and to this mixture was added dropwise 3.3 g of (E)-4-methyl-6-(2'-tetrahydropyranyloxy)-4-hexenal in 20 ml of anhydrous tetrahydrofuran. The mixture was stirred for 30 minutes and cooled to −50° C., and to this was added the equimolar amount of a sec-butyllithium-pentane solution. The temperature was slowly raised to −10° C., and 1.5 g of dry paraformaldehyde was added at once thereto. The reaction mixture was then stirred at room temperature for 2 hours, and, after addition of ice-water, extracted with n-hexane. From the n-hexane extract was obtained 7.2 g of an oil, which was then chromatographed on the silica gel (20 g) column. The resulting oil (5.8 g) was dissolved in 50 ml of a methanol solution containing 100 mg of p-toluenesulfonic acid, and allowed to stand overnight. The mixture was then, after addition of an aqueous sodium hydrogencarbonate solution, extracted with ether. The crude product obtained from the ethereal layer was further purified by the silica gel (30 g) column chromatography, yielding 1.8 g of the desired product.

NMR spectrum δppm (CCl$_4$): 1.58 (6H, S), 1.66 (6H, S), 1.9–2.3 (12H, m), 3.94 (2H, S), 3.97 (2H, d), 5.0–5.3 (4H, m)

IR spectrum νcm$^{-1}$ (liquid): 3300, 1665, 1440, 1380, 1000

EXAMPLE 2

(E,Z,E) and (E,E,E)-7-Hydroxymethyl-3,11,15-trimethyl-2,6,10,14-hexadecatetraen-1-ol (1) In 300 ml of anhydrous tetrahydrofuran was suspended 58.6 g of (E)-4-methyl-6-(2'-tetrahydropyranyloxy)-4-hexen-1-yltriphenylphosphonium iodide [R. Tschesche and J. Reden, Ann. 853 (1974)]. To this suspension was added dropwise the equimolar amount of a n-butyllithium-hexane solution at −20° C. in a stream of nitrogen. The mixture was stirred, and to this was further added 25.4 g of (E)-1,1-dimethoxy-6,10-dimethyl-5,9-undecadien-2-one (prepared in Referential example 1) in 50 ml of anhydrous tetrahydrofuran. The reaction mixture was stirred at room temperature for 3 hours, and, after addition of ice-water, extracted with n-hexane. The so obtained crude oil was suspended in 300 ml of 50% acetic acid, and stirred at room temperature for 2 hours. There was obtained 28.0 g of 7-formyl-3,11,15-trimethyl-2,6,10,14-hexadecatetraen-1-ol tetrahydropyranyl ether from the n-hexane extract. The obtained product was dissolved in 200 ml of ethanol and, after addition of 1.5 g of sodium borohydride, stirred for 2 hours under ice-cooling. This was treated with dilute acetic acid and, after addition of water, extracted with n-hexane. The resultant was dissolved in 200 ml of methanol. To this was added 200 mg of p-toluenesulfonic acid, and the resulting solution was allowed to stand overnight and neutralized with an aqueous sodium hydrogencarbonate solution. After evaporation of the methanol, the residue was extracted with ether, and from the extract was obtained an oil. The so obtained oil was then chromatographed on silica gel to yield 18.2 g of a mixture of the (E,Z,E) and (E,E,E) isomers of 7-hydroxymethyl-3,11,15-trimethyl-2,6,10,14-hexadecatetraen-1-ol.

NMR spectrum δppm (CCl$_4$): 1.58 (6H, S), 1.66 (6H, S), 1.9–2.3 (12H, m), 3.94 (2H, S), 3.97 (2H, d), 5.0–5.3 (4H, m)

IR spectrum νcm$^{-1}$ (liquid): 3300, 1665, 1440, 1380, 1000, 840

(2) In 30 ml of anhydrous tetrahydrofuran was suspended 5.4 g of (E)-4-methyl-6-acetoxy-4-hexen-1-yltriphenylphosphonium iodide, and to this suspension was added dropwise two molar equivalents of a n-butyllithium-hexane solution at −20° C. in a stream of nitrogen. The mixture was stirred at −20° C. for 2 hours, and to this was further added 2.5 g of (E)-6,10-dimethyl-2-oxo-5,9-undecadien-1-ol acetate (prepared in Referential example 2) in 10 ml of anhydrous tetrahydrofuran. The resulting mixture was again stirred at room temperature for 3 hours and, after addition of ice-water, extracted with ether, and from the extract was obtained an oil. The so obtained crude oil was dissolved in 25 ml of a 5% potassium hydroxide-ethanol solution under ice-cooling, and allowed to stand for 2 hours. This was, after addition of water, extracted with ether and treated in the usual way. The resultant was then chromatographed on silica gel to yield 0.95 g of the desired product.

(3) In 10 ml of dimethoxyethane was suspended 0.75 g of 50% sodium hydride, and this suspension was, after addition of 4.5 g of triethyl phosphonoacetate, stirred for 30 minutes. To this mixture was added 5.6 g of homogeranyl iodide, and the reaction proceeded at 50° C. for 2 hours. The reaction mixture was then cooled to 0°–5° C. and, after addition of 0.75 g of 50% sodium hydride, stirred at room temperature for one hour. To this mixture was added 3.4 g of (E)-6-acetoxy-4-methyl-4-heptenal, and the reaction proceeded at 50° C. for one hour. The reaction mixture was, after addition of water, extracted with n-hexane. The extract was purified by the silica gel column chromatography to yield 4.7 g of 7-carboethoxy-3,11,15-trimethyl-2,6,10,14-hexadecatetraen-1-ol acetate.

The ester thus obtained was further reduced by aluminum hydride (prepared from 760 mg of lithium aluminum hydride and 880 mg of aluminum chloride) in 7 ml of ether. After completion of the reaction, ethyl acetate was added to the reaction mixture, and the precipitate was filtered off. The filtrate was evaporated to dryness, yielding 3.5 g of the desired product.

EXAMPLE 3

(E,Z,E), (Z,Z,E), (Z,E,E) and (E,E,E)-7-Hydroxymethyl-3,11,15-trimethyl-2,6,10,14-hexadecatetraen-1-ol In 50 ml of anhydrous tetrahydrofuran was suspended 10.78 g of a mixture of the (E) and (Z) isomers of 4-methyl-6-(2'-tetrahydropyranyloxy)-4-hexen-1-yltriphenylphosphonium bromide (E:Z=7:3), and to this suspension was added dropwise the equimolar amount of a n-butyllithium-hexane solution at −20° C. in a stream of nitrogen. The mixture was stirred at −20° C. for one hour, and to this was subsequently added 5.0 g of (E)-1,1-dimethoxy-6,10-dimethyl-5,9-undecadien-2-on in 15 ml of anhydrous tetrahydrofuran. The resulting mixture was stirred at room temperature for 3 hours and treated in the same manner as in Example 2-(1) to give 3.0 g of the desired product.

NMR spectrum δppm (CDCl$_3$): 1.58, 1.64 (12H), 1.9–2.3 (12H), 3.95, 4.02, 4.08 (4H, m), 5.9–6.6 (4H, m)

IR spectrum νcm$^{-1}$ (liquid): 3325, 1665, 1440, 1380, 1000

EXAMPLE 4

(E,Z,E) and (E,E,E)-7-Hydroxymethyl-3,11,15-trimethyl-2,6,10,14-hexadecatetraen-1-ol diacetate In 5 ml of anhydrous pyridine was dissolved 1.0 g of 7-hydroxymethyl-3,11,15-trimethyl-2,6,10,14-hexadecatetraen-1-ol, and the solution was, after addition of 2 ml of acetic anhydride, allowed to stand overnight at room temperature. The reaction mixture was then poured into ice-water and extracted with ether. The ethereal layer was washed successively with an aqueous sodium hydrogencarbonate, dilute hydrochloric acid and water. Upon evaporation, 1.1 g of the desired diacetate was obtained.

NMR spectrum δppm (CDCl$_3$): 1.58 (3H, s), 1.62 (3H, s), 1.70 (6H, s), 2.07 (6H, s), 1.8–2.4 (12H, m), 4.60 (2H, d), 4.67 (2H, s), 4.9–5.6 (4H, m)

IR spectrum νcm$^{-1}$ (liquid): 1740, 1445, 1370, 1235, 1025, 960

EXAMPLE 5

(E,Z,E)- and (E,E,E)-7-Hydroxymethyl-3,11,15-trimethyl-2,6,10,14-hexadecatetraen-1-ol dibenzoate In 5 ml of anhydrous pyridine was dissolved 1.0 g of 7-hydroxymethyl-3,11,15-trimethyl-2,6,10,14-hexadecatetraen-1-ol, and to this solution was added 1.0 ml of benzoyl chloride. After standing overnight at room temperature, the reaction mixture was treated in the same manner as in Example 4 with regard to the diacetate to yield 1.5 g of the dibenzoate.

NMR spectrum δppm (CCl$_4$): 1.53 (6H, s), 1.60 (3H, s), 1.80 (3H, s), 1.8–2.4 (12H, m), 4.69 (2H, d), 4.76 (2H, s), 5.0–5.4 (4H, m), 7.2–7.4 (6H, m), 8.0 (4H, m)

IR spectrum νcm$^{-1}$ (liquid):
1720, 1603, 1590, 1450, 1380, 1315, 1270, 1175, 1105, 1070, 1030, 940, 710, 685

EXAMPLE 6

(E,Z,E)- and (E,E,E)-7-Hydroxymethyl-3,11,15-trimethyl-2,6,10,14-hexadecatetraen-1-ol dilaurate In 5 ml of anhydrous pyridine was dissolved 1.0 g of 7-hydroxymethyl-3,11,15-trimethyl-2,6,10,14-hexadecatetraen-1-ol, and to this solution was added 2 ml of lauroyl chloride. After standing overnight at room temperature, the reaction mixture was treated in the same manner as in Example 4 to yield 1.8 g of the dilaurate.

NMR spectrum δppm (CCl$_4$): 0.85 (6H, m), 1.2 (40H, m), 1.55 (12H, s), 1.8–2.4 (12H, m), 4.35 (2H, d), 4.42 (2H, s), 4.9–5.4 (4H, m)

IR spectrum νcm$^{-1}$ (liquid): 1738, 1670, 1460, 1380, 1160, 1108, 960

EXAMPLE 7

(E,Z,E) and (E,E,E)-7-Hydroxymethyl-3,11,15-trimethyl-2,6,10,14-hexadecatetraen-1-ol di-n-caproate In 5 ml of anhydrous pyridine was dissolved 300 mg of 7-hydroxymethyl-3,11,15-trimethyl-2,6,10,14-hexadecatetraen-1-ol, and to this solution was added 0.5 ml of n-caproic anhydride. After standing overnight at room temperature, the reaction mixture was added into ice-water and extracted with n-hexane. The extract was then treated in the same manner as in Example 4 to yield 300 mg of the desired di-n-caproate.

NMR spectrum δppm (CCl$_4$): 0.86 (6H, t), 1.3 (8H, m), 1.48 (6H, s), 1.55 (3H, s), 1.60 (3H, s), 4.35 (2H, d), 4.40 (2H, s), 4.8–5.3 (4H, m)

IR spectrum νcm$^{-1}$ (liquid): 1740, 1670, 1450, 1380, 1310, 1270, 1240, 1170, 1105, 1090, 980, 840

EXAMPLE 8

(E,Z,E) and (E,E,E)-7-Hydroxymethyl-3,11,15-trimethyl-2,6,10,14-hexadecatetraen-1-ol dicrotonate In 2 ml of pyridine was dissolved 300 mg of 7-hydroxymethyl-3,11,15-trimethyl-2,6,10,14-hexadecatetraen-1-ol, and to this solution was added 0.5 ml of crotonic anhydride. After standing overnight at room temperature, the reaction mixture was poured into ice-water and extracted with n-hexane. The extract was then treated in the same manner as in Example 4 to yield 100 mg of the desired dicrotonate.

NMR spectrum δppm (CCl$_4$): 1.59 (6H, s), 1.65 (3H, s), 1.71 (3H, s), 1.89 (6H, d), 4.0 (2H, s), 4.53 (2H, d), 5.0 (4H, m), 5.73 (2H, d), 6.85 (2H, m)

IR spectrum νcm$^{-1}$ (liquid):
1720, 1700, 1660, 1440, 1380, 1310, 1295, 1260, 1180, 1100, 1005, 970, 840, 785, 760

EXAMPLE 9

(E,Z,E) and (E,E,E)-7-Hydroxymethyl-3,11,15-trimethyl-2,6,10,14hexadecatetraen-1-ol dicinnamate In 2 ml of pyridine was dissolved 300 mg of 7-hyroxymethyl-3,11,15-trimethyl-2,6,10,14-hexadecatetraen-1-ol, and to this solution was added 0.5 ml of cinnamoyl chloride. After standing overnight at room temperature, the reaction mixture was poured into ice-water and extracted with n-hexane. The extract was then treated in the same manner as in Example 4 to yield 300 mg of the desired dicinnamate.

NMR spectrum δppm (CCl$_4$): 1.49 (6H, s), 1.55 (3H, s), 1.67 (3H, s), 4.55 (2H, d), 4.6 (2H, s), 5.0 (2H, m), 5.3 (2H, m), 6.25 (2H, d), 7.2 (10H, m), 7.5 (2H, d)

IR spectrum νcm$^{-1}$ (liquid): 1710, 1640, 1580, 1500, 1450, 1380, 1325, 1305, 1280, 1250, 1200, 1160, 1100, 1070, 1000, 980, 860, 765, 708, 680

EXAMPLE 10

(E,Z,E)-7-Hydroxymethyl-3,11,15-trimethyl-2,6,10,14-hexadecatetraen-1-ol dimethyl ether In 10 ml of N,N-dimethylformamide was dissolved 1 g of 7-hydroxymethyl-3,11,15-trimethyl-2,6,10,14-hexadecatetraen-1-ol. To this solution were added 2 ml of methyl iodide and 3 g of silver oxide, and the mixture was vigorously stirred at room temperature for 16 hours. An excess of methyl iodide was distilled off, and the residue was, after addition of water, extracted with n-hexane. The n-hexane layer was washed with water and dried. The solvent was distilled off, and the residual oil was chromatographed on silica gel, yielding 900 mg of the desired dimethyl ether.

NMR spectrum δppm (CDCl$_3$): 1.56 (6H, s), 1.64 (6H, s), 1.8–2.3 (12H, m), 3.26 (6H, s) 3.85 (2H, s), 3.86 (2H, d), 4.8–5.4 (4H, m)

IR spectrum νcm$^{-1}$ (liquid):
1680, 1455, 1390, 1100, 960, 920

EXAMPLE 11

(E,E,E)-7-Hydroxymethyl-3,11,15-trimethyl-2,6,10,14-hexadecatetraen-1-ol

In 100 ml of methanol was dissolved 10.0 g of 7-formyl-3,11,15-trimethyl-2,6,10,14-hexadecatetraen-1-ol tetrahydropyranyl ether prepared in Example 2-(1), and to this solution was added 100 mg of p-toluenesulfonic acid. The mixture was allowed to stand overnight at room temperature and neutralized with an aqueous sodium hydrogencarbonate solution. The methanol was distilled off, and the residue was extracted with ether. (E,E,E)-7-Formyl-3,11,15-trimethyl-2,6,10,14-hexadecatetraen-1-ol obtained from the ethereal layer was dissolved in 60 ml of ethanol. After addition of 5.5 g of sodium borohydride under ice-cooling, the solution was vigorously stirred for 2 hours. The mixture was then treated with dilute acetic acid and, after addition of water, extracted with ether. The oil obtained from the ethereal layer was purified by the silica gel column chromatography, yielding 6.6 g of the desired (E,E,E)-7-hydroxymethyl-3,11,15-trimethyl-2,6,10,14-hexadecatetraen-1-ol.

NMR spectrum δppm (CDCl$_3$): 1.51 (6H, s), 1.58 (6H, s), 1.8–2.2 (12H, m), 3.95 (2H, s), 4.05 (2H, d), 5.0–5.3 (4H, m)

IR spectrum νcm$^{-1}$ (liquid): 3300, 1670, 1440, 1380, 1000, 840

EXAMPLE 12

(E,E,E)-7-Hydroxymethyl-3,11,15-trimethyl-2,6,10,14-hexadecatetraen-1-ol diacetate The acetylation stated in Example 4 was repeated using 1 g of (E,E,E)-7-hydroxymethyl-3,11,15-trimethyl-2,6,10,14-hexadecatetraen-1-ol, to yield 1.0 g of the desired diacetate.

NMR spectrum δppm (CCl$_4$): 1.60 (6H, s), 1.66 (3H, s), 1.71 (3H, s), 1.97 (3H, s), 2.00 (3H, s), 1.9–2.2 (12H, m), 4.45 (2H, s), 4.50 (2H, d), 4.9–5.5 (4H, m)

IR spectrum νcm$^{-1}$ (liquid): 1750, 1680, 1445, 1385, 1375, 1240, 1030, 960

EXAMPLE 13

(Z,E,E)-7-Hydroxymethyl-3,11,15-trimethyl-2,6,10,14-hexadecatetraen-1-ol

In 250 ml of anhydrous tetrahydrofuran was suspended 37.2 g of (Z)-4-methyl-6-acetoxy-4-hexen-1-yltriphenylphosphonium iodide, and to this suspension was added dropwise two molar equivalents of a n-butyllithium-hexane solution at −20° C. in a stream of nitrogen. The resulting mixture was stirred at −20° C. for one hour, and to this was further added 19.0 g of (E)-11-diethoxy-6,10-dimethyl-5,9-undecadien-2-one in 50 ml of anhydrous tetrahydrofuran. The mixture was then stirred at room temperature for 3 hours and, after addition of ice-water, extracted with n-hexane and from the extract was obtained an oil. The crude oil was hydrolyzed with an alcoholic sodium hydroxide (5%) and treated with 50% acetic acid at room temperature for 2 hours. The so obtained product was dissolved in 100 ml of n-hexane and, after addition of 100 g of calcium chloride, shaken vigorously at room temperature. The resulting calcium chloride adduct was decomposed with water and extracted with n-hexane to yield (Z,E,E)-7-formyl-3,11,15-trimethyl-2,6,10,14-hexadecatetraen-1-ol. This product was dissolved in 200 ml of ethanol and, after addition of 1 g of sodium borohydride under ice-cooling, stirred for 2 hours. The mixture was then treated with dilute acetic acid and, after addition of water, extracted with ether. The ethereal extract was purified by the alumina (120 g) column chromatography to yield 5.8 g of the desired product.

NMR spectrum δ ppm (CDCl$_3$): 1.50 (6H, s), 1.57 (3H, s), 1.61 (3H, s), 1.8–2.2 (12H, m), 3.85 (2H, s), 3.91 (2H, d), 5.0–5.3 (4H, m)

IR spectrum ν cm$^{-1}$ (liquid): 3300, 1665, 1440, 1380, 1000, 840

EXAMPLE 14

(E,Z,Z) and (E,E,Z)-7-Hydroxymethyl-3,11,15-trimethyl-2,6,10,14-hexadecatetraen-1-ol In 125 ml of anhydrous tetrahydrofuran was suspended 18 g of (E)-4-methyl-(-acetoxy-4-hexen-1-yltriphenylphosphonium iodide, and to this suspension was added dropwise two molar equivalents of a n-butyllithium-hexane solution at −20° C. in a stream of nitrogen.

The resulting mixture was stirred at −20° C. for one hour and to this was further added 8.4 g of (Z)-1,1-diethoxy-6,10-dimethyl-5,9-undecadien-2-one (prepared in Referential example 3) in 25 ml of anhydrous tetrahydrofuran. The mixture was then stirred at room temperature for 3 hours and, after addition of ice-water, extracted with n-hexane, and from the extract was obtained an oil. The oil was treated with a sodium hydroxide solution and acetic acid and reduced with 150 mg of sodium borohydride in the same manner as in Example 13, yielding 3.0 g of a mixture of the (E,Z,Z) and (E,E,Z) isomers.

NMR spectrum δ ppm (CDCl$_3$): 1.73 (3H, s), 1.78 (9H, s), 1.8–2.4 (12H, m), 4.18 (2H, s), 4.25 (2H, d), 5.2–5.5 (4H, m)

IR spectrum ν cm$^{-1}$ (liquid): 3350, 1670, 1450, 1385, 1005, 830

EXAMPLE 15

11-Hydroxymethyl-3,7,15-trimethyl-2,6,10,14-hexadecatetraen-1-ol

In 120 ml of anhydrous tetrahydrofuran was suspended 23.1 g of (E)-4-methyl-6-(2'-tetrahydropyranyloxy)-4-hexen-1-yltriphenylphosphonium iodide. In the same manner as in Example 2-(1), the equimolar amount of n-butyllithium and 7.2 g of 6-acetoxymethyl-10-methyl-5,9-undecadien-2-one prepared in Referential Examples 4 and 5 were added to the suspension, and the Wittig reaction was carried out. The product was hydrolyzed with 70 ml of an alcoholic sodium hydroxide (5%) and treated overnight with methanol containing 100 mg of p-toluenesulfonic acid at room temperature. This was then purified by the silica gel (100 g) column chromatography to yield 3.7 g of the desired product, which was a mixture of the (E,E,E), (E,Z,Z), (E,Z,E) and (E,E,Z) isomers.

NMR spectrum δ ppm (CDCl$_3$): 1.60 (6H, s), 1.70 (6H, s), 1.8–2.4 (12H, m), 4.13 (2H, s), 4.13 (2H, d), 5.0–5.4 (4H, m)

IR spectrum ν cm$^{-1}$ (liquid): 3350, 1670, 1440, 1380, 1010, 840

EXAMPLE 16

(E,Z) and (E,E)-7-Hydroxymethyl-3,11-dimethyl-2,6,10-dodecatrien-1-ol

In 20 ml of anhydrous dimethoxyethane was suspended 1.5 g of 50% sodium hydride, and the suspension was, after addition of 8.9 g of triethyl phosphonoacetate, stirred at room temperature for one hour. To this mixture was added 6.5 g of 4-methyl-3-pentenyl bromide, and the reaction was carried out at 50° C. for 3 hours. The reaction mixture was cooled to 0°–5° C. and, after addition of 1.5 g of 50% sodium hydride, stirred at room temperature for one hour. Subsequently, 6.8 g of (E)-6-acetoxy-4-methyl-4-hexenal was added to the reaction mixture, and the reaction was carried out for one hour. The reaction mixture was, after addition of water, extracted with n-hexane. The extract was chromatographed on silica gel to 2.2 g of 7-carboethoxy-3,11-dimethyl-2,6,10-dodecatrien-1-ol acetate.

The ester thus obtained was reduced with aluminum hydride (prepared from 380 mg of lithium aluminum hydride and 440 mg of aluminum chloride) in ether to yield 780 mg of the desired product.

NMR spectrum δ ppm (CDCl$_3$): 1.60 (3H, s), 1.68 (6H, s), 2.1 (8H, m), 4.08 (2H, s), 4.10 (2H, d), 5.2–5.4 (3H, m)

IR spectrum ν cm$^{-1}$ (liquid): 3350, 1670, 1375, 1240, 1000, 830

EXAMPLE 17

(E,Z,E,E) and (E,E,E,E)-7,15-Hydroxymethyl-3,11-dimethyl-2,6,10,14-hexadecatetraen-1-ol The conventional acetylation was carried out on 11,11-diethoxy-2,6-dimethyl-10-oxo-2,6-undecadien-1-ol prepared by the process stated in Referential example 6, and the resulting acetate (9 g) was treated with 16.3 g of (E)-4-methyl-6-(2'-tetrahydropyranyloxy)-4-hexen-1-yltriphenylphosphonium iodide which had previously been treated with n-butyllithium in 100 ml of anhydrous tetrahydrofuran. The product was then hydrolyzed with 1 g of sodium carbonate in methanol and stirred in 80 ml of 50% acetic acid at room temperature for 3 hours, whereby hydrolysis of the acetal was carried out. The so obtained product having the formyl group was reduced with 200 mg of sodium borohydride in 50 ml of ethanol. Subsequently, treatment tetrahydropyranyl group of the product was liberated by treatment with p-toluenesulfonic acid in methanol in the usual way. The oil (2.4 g) thus obtained was purified by the silica gel column chromatography to yield 1.0 g of the desired triol.

NMR spectrum δ ppm (CDCl$_3$) 1.65 (9H, s), 2.1 (12H, m), 4.0–4.2 (6H, m), 5.1–5.4 (4H, m)

IR spectrum ν cm$^{-1}$ (liquid): 3350, 1670, 1440, 1380, 1230, 1060, 1000, 940

EXAMPLE 18

7-Hydroxymethyl-3,11,15,19-tetramethyl-2,6,10,14,18-eicosapentaen-1-ol

Following the procedure stated in Example 2-(1), 5.8 g of (E)-4-methyl-6-(2'-tetrahydropyranyloxy)-4-hexen-1-yltriphenylphosphonium iodide was treated with n-butyllithium in 30 ml of anhydrous tetrahydrofuran. Then, the resultant was treated with 3.2 g of 1,1-dimethoxy-6,10,14-trimethyl-5,9,13-pentadecatrien-2-one prepared by the process stated in Referential example 7. The resulting oil was treated with 40 ml of 50% acetic acid to yield 4.2 g of 7-formyl-3,11,15,19-tetramethyl-2,6,10,14,18-eicosapentaen-1-ol tetrahydropyranyl ether. The product was reduced with 150 mg of sodium borohydride and treated with p-toluenesulfonic acid in methanol in the same manner as stated earlier, and purified by the silica gel column chromatography to yield 1.6 g of the desired product. This was a mixture of the (E,E,E,E), (E,Z,Z,E), (E,Z,E,E) and (E,E,Z,E) isomers.

NMR spectrum δ ppm (CDCl$_3$): 1.50 (9H, s), 1.58 (6H, s), 1.8–2.7 (16H, m), 3.98 (2H, s), 4.00 (2H, d), 4.9–5.4 (5H, m)

IR spectrum ν cm$^{-1}$ (liquid): 3350, 1670, 1445, 1380, 1000, 830

EXAMPLE 19

7-Hydroxymethyl-3,11,15,19-tetramethyl-2,6,10,14,18-eicosapentaen-1-ol diacetate In 5 ml of anhydrous pyridine, 500 mg of 7-hydroxymethyl-3,11,15,19-tetramethyl-2,6,10,14,18-eicosapentaen-1-ol was acetylated with 0.5 ml of acetic anhydride. The resultant was treated in the same manner as in Example 4 to yield 300 mg of the desired diacetate.

NMR spectrum δ ppm (CCl$_4$): 1.50–1.61 (15H, s), 1.90 (3H, s), 1.92 (3H, s), 1.8–2.4 (16H, m), 4.34 (2H, s), 4.41 (2H, d), 4.8–5.4 (5H m)

IR spectrum ν cm$^{-1}$ (liquid): 1750, 1690, 1390, 1385, 1238, 1025, 960, 840

EXAMPLE 20

7-Hydroxymethyl-3,11,15,19-tetramethyl-2,6,10,14,18-eicosapentaen-1-ol dibenzoate In 5 ml of anhydrous pyridine, 230 mg of 7-hydroxymethyl-3,11,15,19-tetramethyl-2,6,10,14,18-eicosapentaen-1-ol was benzoylated with 0.5 ml of benzoyl chloride. The resultant was then treated in the same manner as in Example 5 to yield 280 mg of the desired dibenzoate.

NMR spectrum δ ppm (CCl$_4$): 1.55 (9H, s), 1.62 (3H, s), 1.75 (3H, s), 1.9–2.2 (16H, m), 4.70 (2H, d), 4.77 (2H, s), 5.0–5.4 (5H, m), 7.3 (6H, m), 7.90 (4H, m)

IR spectrum ν cm$^{-1}$ (liquid): 1725, 1680, 1610, 1590, 1455, 1390, 1320, 1275, 1180, 1110, 1075, 1030, 950, 940, 840, 710, 690

REFERENTIAL EXAMPLE 1

(E)-1,1-Dimethoxy-6,10-dimethyl-5,9-undecadien-2-one

In 350 ml of anhydrous ethanol was dissolved 17.4 g of sodium metal, and to this was added dropwise 160 g of methyl 4,4-dimethoxyacetoacetate with stirring at room temperature. One hour later, geranyl bromide prepared from 130 g of geraniol was added dropwise to the above-obtained mixture under ice-cooling. The mixture was then allowed to stand overnight at room temperature and refluxed for one hour. To this reaction mixture was added 42 g of sodium hydroxide in a mixture of 1.4 l. of ethanol and 1.18 l. of water, and the mixture was heated under reflux for 6 hours and extracted with n-hexane. The n-hexane extract was distilled under reduced pressure to give 134 g of the desired product, b.p. 92°–95° C./0.05 mmHg.

NMR spectrum δ ppm (CDCl$_3$): 1.58 (6H, s), 1.62 (3H, s), 1.8–2.7 (8H, m), 3.35 (6H, s), 4.39 (1H, s), 5.05 (2H, m)

IR spectrum ν cm$^{-1}$ (liquid): 1735, 1075, 1000

REFERENTIAL EXAMPLE 2

(E)-6,10-Dimethyl-2-oxo-5,9-undecadien-1-ol acetate

To 19.6 g of geranylacetic acid was added 32 g of oxalyl chloride, and, after standing overnight at room temperature, the mixture was evaporated under reduced pressure to remove an excess of the reagent. The resulting acid chloride was dissolved in 100 ml of ether and added dropwise to an ethereal solution containing 0.2 mole of diazomethane under ice-cooling. After completion of the reaction, the ether was removed by evaporation. The resulting diazoketone was dissolved in 100 ml of acetic acid and heated at 90° C. for 5 hours. The reaction mixture was diluted with water and extracted with ether. The ethereal layer was washed successively with an aqueous sodium hydrogencarbonate solution and water, dried and evaporated to remove the solvent. The residual oil was distilled under reduced pressure to give 15.0 g of the desired product, b.p. 132° C./0.02 mmHg.

NMR spectrum δ ppm (CDCl$_3$): 1.56 (9H, s), 2.05 (3H, s), 4.45 (2H, s), 4.8–5.3 (2H, s)

IR spectrum ν cm$^{-1}$ (liquid): 1755, 1740, 1375, 1230, 1060

REFERENTIAL EXAMPLE 3

(Z)-1,1-Diethoxy-6,10-dimethyl-5,9-undecadien-2-one

Reaction of neryl bromide which had been prepared from 31 g of nerol with 41.5 g of ethyl 4,4-diethoxyacetoacetate was carried out in the same manner as in Referential example 1 to yield 20 g of the desired product, b.p. 122° C./0.02 mmHg.

NMR spectrum δ ppm (CDCl$_3$): 1.32 (6H, t), 1.65 (3H, s), 1.74 (6H, s), 1.8–2.7 (8H, m), 3.71 (4H, m), 4.61 (1H, s), 5.19 (2H, m)

IR spectrum ν cm$^{-1}$ (liquid): 1735, 1075, 1000

REFERENTIAL EXAMPLE 4

1,1-Diethoxy-6-methyl-5-hepten-2-one

Following the procedure stated in Referential example 1, reaction of 7.3 g of ethyl 4,4-diethoxyacetoacetate with 4.0 g of 3-methyl-2-butenyl chloride was carried out in the presence of sodium ethoxide and the resultant was decarboxylated with the alcoholic sodium hydroxide to yield 4.1 g of the desired product, b.p. 102°–103° C./1 mmHg.

NMR spectrum δ ppm (CCl$_4$): 1.19 (3H, t), 1.60 (3H, s), 1.63 (3H, s), 2.42 (4H, m), 3.55 (4H, m), 4.31 (1H, s), 5.02 (1H, t)

IR spectrum ν cm$^{-1}$ (liquid): 1730, 1445, 1400, 1380, 1315, 1150, 1100, 1060, 900, 830, 745

REFERENTIAL EXAMPLE 5

(E) and (Z)-6-Acetoxymethyl-10-methyl-5,9-undecadien-2-one

In 160 ml of anhydrous tetrahydrofuran was suspended 38.5 g of 4,4-ethylenedioxypentan-1-yltriphenylphosphonium bromide, and to this was added the equimolar amount of a n-butyllithium-hexane solution at −20° C. in a stream of nitrogen. The reaction mixture was stirred for one hour and cooled to −60° C. To this was added 14.5 g of 1,1-diethoxy-6-methyl-5-hepten-2-one, and the resulting mixture was stirred at room temperature for 3 hours. The reaction mixture was, after addition of icewater, extracted with n-hexane and from the extract was obtained an oil. The oil was suspended in 250 ml of 50% acetic acid and stirred at room temperature for one hour. 2,2-Ethylenedioxy-6-formyl-10-methyl-5,9-undecadiene obtained by the n-hexane extraction, not purified, was reduced in 100 ml of ethanol by using 500 mg of sodium borohydride. The product thus obtained was chromatographed on the silica gel (100 g) column to yield 7.3 g of 2,2-ethylenedioxy-6-hydroxymethyl-10-methyl-5,9-undecadien.

NMR spectrum δ ppm (CDCl$_3$): 1.19 (3H, s), 1.47 (3H, s), 1.58 (3H, s), 3.75 (4H, s), 3.91 (2H, s), 5.0–5.3 (2H, m)

IR spectrum ν cm$^{-1}$ (liquid): 3450, 1680

7.2 g of the alcohol thus obtained was acetylated with anhydrous pyridine-acetic anhydride in the usual way and dissolved in 70 ml of methanol. To this solution was added 70 mg of p-toluenesulfonic acid, and the mixture was allowed to stand overnight at room temperature. The resultant was neutralized with an aqueous sodium hydrogencarbonate solution and extracted with n-hexane. There was obtained 7.2 g of the desired product.

NMR spectrum δ ppm (CDCl₃): 1.50 (3H, s), 1.58 (3H, s), 1.91 (3H, s), 1.99 (3H, s), 4.32 and 4.47 (E and Z) (2H, s), 5.0–5.3 (2H, m)

IR spectrum ν cm⁻¹ (liquid): 1740, 1720, 1440, 1370, 1230, 1160, 1050, 1025, 960, 830

REFERENTIAL EXAMPLE 6

(E,E)-11,11-Diethoxy-2,6-dimethyl-10-oxo-2,6-undecadien-1-ol

In 70 ml of 95% ethanol was dissolved 7.4 g of 1,1-diethoxy-6,10-dimethyl-2-oxo-5,9-undecadien, and the resulting solution was, after addition of 1.7 g of selenium oxide, refluxed for 15 minutes. The ethanol was removed by evaporation, and the residue was, after addition of water, extracted with ether. The ethereal extract was washed with an aqueous sodium hydrogencarbonate solution and dried. The solvent was then removed by evaporation to leave an oil, and the oil was purified by the silica gel column chromatography to yield 3.0 g of the desired product.

NMR spectrum δ ppm (CCl₄): 1.20 (6H, t), 1.50 (6H, s), 3.5 (4H m), 3.80 (2H, br. s), 4.32 (1H, s), 5.0–5.3 (2H, m)

IR spectrum ν cm⁻¹ (liquid): 3500, 1740, 1450, 1380, 1325, 1250, 1160, 1105, 1070, 1020, 900

REFERENTIAL EXAMPLE 7

(E,E) and (Z,E)-1,1-Dimethoxy-6,10,14-trimethyl-5,9,13-pentadecatrien-2-one

Following the procedure stated in Referential example 1, reaction of farnesyl bromide which had been prepared from 22 g of nerolidol with 19 g of methyl 4,4-dimethoxyacetoacetate was carried out and the reaction mixture was purified by the silica gel (200 g) column chromatography to yield 12.8 g of the desired product.

NMR spectrum δ ppm (CDCl₃): 1.47 (9H, s), 1.54 (3H, s), 1.8–2.7 (12H, m), 3.28 (6H, s), 4.30 (1H, s), 4.98 (3H, m)

IR spectrum ν cm⁻¹ (liquid): 1742, 1460, 1390, 1230, 1200, 1118, 1080, 1000, 960, 845

What is claimed is:

1. A compound having the formula

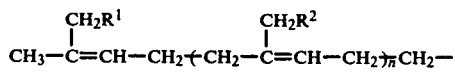

-continued

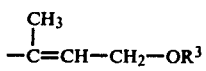

in which R¹ and R² may be the same or different and each represents a hydrogen atom, hydroxyl, alkoxy having from 1 to 8 carbon atoms, aliphatic acyloxy having from 2 to 18 carbon atoms, aromatic acyloxy or araliphatic acyloxy having from 2 to 3 carbon atoms in the aliphatic acyl moiety, R³ represents alkyl having from 1 to 8 carbon atoms, n is an integer of from 1 to 4 and, when n is an integer of from 2 to 4, the R²'s may be the same or different; provided that, when n is 1 or 2, at least one of R¹ and R² is hydroxyl, alkoxy, aliphatic acyloxy, aromatic acyloxy or araliphatic acyloxy.

2. A compound according to claim 1 wherein R¹ and R² may be the same or different and each represents a hydrogen atom, hydroxyl, alkoxy having from 1 to 4 carbon atoms, aliphatic acyloxy having from 2 to 12 carbon atoms, benzoyloxy or cinnamoyloxy, R³ represents alkyl having from 1 to 4 carbon atoms, n is an integer of from 1 to 3 and, when n is 2 or 3, the R²'s may be the same or different; provided that, when n is 1 or 2, at least one of R¹ and R² is hydroxyl, alkoxy, aliphatic acyloxy, benzoyl or cinnamoyloxy.

3. A compound according to claim 1 wherein R¹ represents a hydrogen atom, R² represents a hydrogen atom, hydroxy, alkoxy having from 1 to 4 carbon atoms, aliphatic acyloxy having from 2 to 12 carbon atoms, benzoyloxy or cinnamoyloxy, R³ represents alkyl having from 1 to 4 carbon atoms, and n is an integer of from 1 to 3; provided that, when n is 1, R² is other than a hydrogen atom and, when n is 2 or 3, at least one of the R²'s is other than a hydrogen atom.

4. A compound according to claim 1 wherein R¹ represents a hydrogen atom, the R² in the side chain at the 7-position of the structural formula represents hydroxyl, alkoxy having from 1 to 2 carbon atoms, aliphatic acyloxy having from 2 to 12 carbon atoms, benzoyloxy or cinnamoyloxy, R³ represents alkyl having from 1 to 2 carbon atoms, and n is an integer of from 1 to 3.

5. 7-Hydroxymethyl-3,11,15-trimethyl-2,6,10,14-hexadecatetraen-1-ol dimethyl ether of the formula of claim 1.

6. (E,Z,E)-7-Hydroxymethyl-3,11,15-trimethyl-2,6,10,14-hexadecatetraen-1-ol dimethyl ether of the formula of claim 1.

* * * * *

UNITED STATES PATENT AND TRADEMARK OFFICE
CERTIFICATE OF CORRECTION

PATENT NO. : 4,192,953
DATED : March 11, 1980
INVENTOR(S) : HIROSHI MISHIMA et al It is certified that error appears in the above-identified patent and that said Letters Patent are hereby corrected as shown below:

Abstract, fifth line from the bottom: replace "$R^2$ and $R^2$'s" with ---$R^1$ and $R^2$'s---.

Column 1, line 22: replace "2 - 8 carbon atoms" with ---2 - 18 carbon atoms---.

Column 4, line 58: replace "S. Ckabe" with ---S. Okabe---.

Column 4, line 63: replace "$2 \pm 1°C.$" with ---$23 \pm 1°C.$---.

Signed and Sealed this

Twenty-ninth Day of July 1980

[SEAL]

Attest:

SIDNEY A. DIAMOND

Attesting Officer     Commissioner of Patents and Trademarks